United States Patent [19]

Sakagami

[11] 4,444,598
[45] Apr. 24, 1984

[54] METHOD FOR WASHING REACTION TUBE

[75] Inventor: Toshio Sakagami, Chofu, Japan

[73] Assignee: Olympus Optical Company Limited, Japan

[21] Appl. No.: 434,872

[22] Filed: Oct. 18, 1982

[30] Foreign Application Priority Data

Oct. 19, 1981 [JP] Japan .............................. 56-165629

[51] Int. Cl.³ ................................................ B08B 9/02
[52] U.S. Cl. .................................. 134/22.12; 134/21; 134/22.18; 422/81; 436/49
[58] Field of Search ...................... 436/49, 53; 422/64, 422/65, 80, 81; 134/21, 22.12, 22.18, 25.4

[56] References Cited

U.S. PATENT DOCUMENTS

| | | | |
|---|---|---|---|
| 3,306,229 | 2/1967 | Smythe | 436/53 X |
| 3,592,605 | 7/1971 | Noma et al. | 422/64 |
| 3,951,605 | 4/1976 | Natelson | 23/253 R |
| 4,227,886 | 10/1980 | Bullock et al. | 134/18 X |
| 4,263,053 | 4/1981 | McKinnon, Jr. | 134/21 |

*Primary Examiner*—S. Leon Bashore, Jr.
*Assistant Examiner*—Joye L. Woodard
*Attorney, Agent, or Firm*—Parkhurst & Oliff

[57] ABSTRACT

A method for washing a U-shaped reaction tube having a thick cup portion and a thin non-cup portion is disclosed. At a first washing position, a washing liquid is supplied into the cup portion of reaction tube like a shower and is simultaneously sucked via the non-cup portion of reaction tube. Then, the washing liquid is supplied again into the reaction tube to fill the tube therewith at a second washing position. Finally, at a third washing position, the washing liquid contained in the reaction tube is drained at such a relatively slow rate that the liquid level of the washing liquid descends slowly. Any drop of the washing liquid is not remained on the inner wall of test tube, and thus it is possible to effect a highly accurate analysis without being affected by contamination between sample solutions.

7 Claims, 1 Drawing Figure

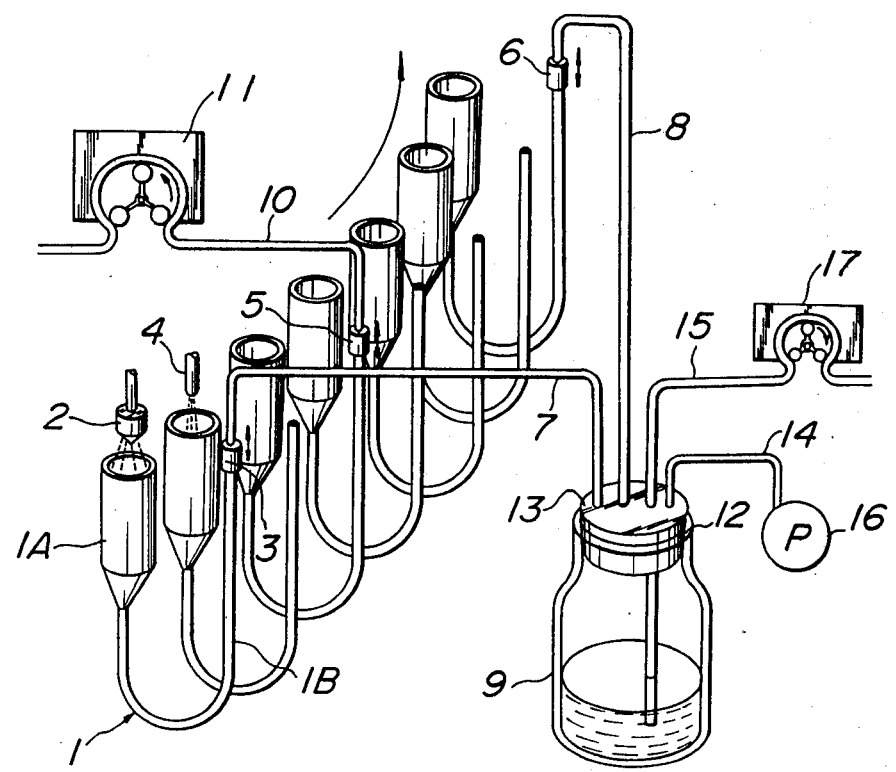

METHOD FOR WASHING REACTION TUBE

BACKGROUND OF THE INVENTION

The present invention relates to a method for washing a reaction tube for use in an automatic analyzer.

As for an automatic analyzer of discrete type, there has been proposed an analyzer wherein a reaction tube for reacting a sample and a reagent supplied therein is used repeatedly. In the automatic analyzer of this kind, in order to prevent contamination between sample solutions to derive accurate analytical results, it is necessary to wash and dry the reaction tube after an analysis for a certain sample solution, but before a start of the analysis for a next sample solution. Up to the present, there have been proposed various washing methods. In one method, the reaction tube is washed by jetting a washing liquid into the reaction tube from its top portion like a shower, while the washing liquid is sucked. In another method, the reaction tube is once filled with the washing liquid and then the washing liquid is sucked by a pump having a relatively large sucking rate per a unit time so as to wash the reaction tube. In the former method, since the washing liquid is jetted into the reaction tube like a shower, it is possible to obtain a relatively high washing efficiency. However, drops of the washing liquid adhered on the inner wall of reaction tube are not sucked sufficiently and thus a highly precise analysis might not be performed. In the latter method, since the washing liquid contained in the reaction tube is sucked at a relatively high rate, a liquid level of the washing liquid in the reaction tube descends abruptly so that drops of the washing liquid are liable to remain on the inner wall of reaction tube and thus, a highly accurate analysis could not be effected.

As explained above, in the known washing methods, it is quite difficult to remove completely the washing liquid from the reaction tube and the remained washing liquid might affect the accuracy of the analysis. This becomes much more serious, because it is now required to decrease amounts of samples and reagents as small as possible.

SUMMARY OF THE INVENTION

The present invention has for its object to eliminate the drawbacks mentioned above and to provide a method for washing a reaction tube for use in an automatic analyzer, which can wash the reaction tube without remaining drops of a washing liquid in the tube and can remove a contamination between sample solutions to improve the analysis accuracy.

According to the invention, a method for washing a reaction tube for use in an automatic analyzer comprises the steps of supplying a washing liquid into said reaction tube like a shower and simultaneously discharging said washing liquid out of said reaction tube at a first rate;

supplying the washing liquid again into said reaction tube to fill the test tube with the washing liquid; and discharging said washing liquid out of said test tube of a second rate which is smaller than the first rate to such an extent that a drop of the washing liquid does not remain on the inner wall of the test tube.

BRIEF DESCRIPTION OF THE DRAWING

FIGURE is a schematic perspective view showing one embodiment of an apparatus for effecting the reaction tube washing method according to the invention.

DESCRIPTION OF THE PREFERRED EMBODIMENTS

FIGURE is a perspective view showing one embodiment of a reaction tube washing apparatus for effecting the washing method according to the invention, which is applied to an automatic analyzer using U-shaped reaction tubes repeatedly. A plurality of U-shaped reaction tubes 1 each comprising a cup portion 1A having a large radius and a non-cupped end portion 1B having a small radius are arranged in a thermostatic vessel (not shown) and are traveled intermittently in a direction shown by an arrow. In this embodiment, a shower nozzle 2 for jetting a washing liquid is arranged at a first washing position which is located on a downstream side viewed in the traveling direction of the reaction tubes 1 with respect to a measuring position at which the sample solution contained in the reaction tube 1 is photometered therethrough or sucked into a photometering flowcell. At the first washing position there is further arranged a first washing liquid discharging end 3 which is detachably coupled with the non-cupped thin end portion 1B. At a second washing position, there is arranged a washing liquid supplying nozzle 4 opposing to the cup portion 1A of the reaction tube 1. At a third washing position, there is arranged a second washing liquid discharging end 5 detachably connected to the end portion 1B of the reaction tube 1. At a fourth position, a suction end 6 is arranged detachably to the end portion 1B of the reaction tube 1. As shown in the drawing, the second, third and fourth positions are separated from the first position by one, two and six pitches, respectively.

The washing liquid discharging end 3 and the suction end 6 are connected to a waste liquid vessel 9 through a waste liquid suction tube 7 and a suction tube 8, respectively, and the washing liquid discharging end 5 is connected to a suction side of a rolling pump 11 rotated at a relatively low speed through a waste liquid suction tube 10. A discharging side of the rolling pump 11 is connected to a waste liquid tank or a drain through a suitable waste liquid tube. Moreover, an opening 12 of the waste liquid vessel 9 is closed airtightly by a plug 13, through which the waste liquid suction tube 7, the suction tube 8, an exhaust tube 14, and a waste liquid discharging tube 15 are inserted into the vessel airtightly. Further, the exhaust tube 14 is connected to a suction side of a vacuum pump 16. In the vessel 9, the waste liquid discharging tube 15 is extended near a bottom of the waste liquid vessel 9 and the other end thereof is connected to a suction side of a rolling pump 17. Moreover, a discharge side of the rolling pump 17 is communicated with the waste liquid tank or the drain.

Now, an operation of the washing apparatus will be explained. In the automatic analyzer, it is assumed that the rolling pumps 11, 17 and the vacuum pump 16 are actuated at the same time. At first, the washing liquid is supplied like a shower into the cup portion 1A of the reaction tube 1 by means of the shower nozzle 2 at the first washing position, and at the same time the washing liquid and remaining sample solution are discharged into the waste liquid vessel 9 via the thin end portion 1B, the discharging end 3 and the suction tube 7 by means of the vacuum pump 16. In this manner, the reaction vessel 1 is once washed. Next, at the second washing position, the washing liquid is supplied to the reaction tube 1 by means of the nozzle 4 to fill the reaction tube 1 therewith. Then, at the third washing position, the washing liquid contained in the reaction tube 1 is sucked by the rolling pump 11 via the waste liquid suction tube 10 at a relatively slow rate, so that the reaction tube 1 is washed again. After that, at the fourth drying position, an air is sucked through the reaction tube 1, the suction end 6 and the suction tube 8 by means of the vacuum pump 16 so as to dry the inner wall of the reaction tube 1 by means of the air stream. The waste liquid gathered in the waste liquid vessel 9 is discharged through the discharging tube 15 by means of the rolling pump 17.

As mentioned above according to the invention, since the reaction tube is first washed effectively by the shower of washing liquid, then is filled with the washing liquid, and is finally sucked at such a slow rate that the liquid level of the washing liquid descends slowly. In case of using the reaction tube made of plastics having an inner diameter of 8 mm of the cup portion 1A, a typical value of the descending speed of the washing liquid level is about 8 mm per second. In case of using the reaction tube made of glass, a lower descending speed may be adopted. Therefore, any drop of the washing liquid does not remain or adhere on the inner wall of tube, so that almost all the washing liquid can be removed from the reaction tube without remaining traces of the washing liquid even if the drops of the washing liquid are remained on the inner upper portion of the reaction tube after the first washing. After that, the air flow is passed through the reaction tube to dry the inner wall of the reaction tube and thus it is possible to always effect a highly accurate analysis without causing contamination between sample solutions.

The present invention is not limited to the embodiments mentioned above, but various alternations and modifications are possible. For example, in the embodiment mentioned above, use is made of the U-shaped reaction tube, but it is possible to use usual straight test tubes. Moreover, this invention is preferably applied to the reaction tube made of glass or plastics, but if use is made of the reaction tube made of plastics having a high hydrophilic property, it is possible to discharge the washing liquid more accurately. In such a case, the last drying step may be deleted. Further, in the above embodiment, the washing liquid supplying nozzle 4 is arranged to oppose to the cup portion 1A, but it is also possible to selectively couple the supplying nozzle 4 with the non-cupped end portion 1B so as to supply the washing liquid therefrom. Furthermore, it is possible to delete the washing liquid supplying nozzle 4 by supplying the washing liquid into the reaction tube 1 by means of the shower nozzle 2. In such a case, after washing the reaction tube 1 by performing simultaneously the washing liquid supplying operation from the shower nozzle 2 and the sucking operation from the discharging end 3, only the sucking operation may be stopped. Moreover, the washing liquid contained in the reaction tube 1 may be sucked into the waste liquid vessel 9 at a relatively slow rate by means of the vacuum pump 16 instead of the rolling pump 11. In this case, in order to decrease the sucking efficiency, an inner diameter of a tube to be connected between the test tube 1 and the vessel 9 may be about a half of that of the tube 7.

What is claimed is:

1. A method for washing a reaction tube for use in an automatic analyzer comprising the steps of
   supplying a washing liquid into said reaction tube like shower and simultaneously discharging said washing liquid out of said reaction tube at a first rate;
   supplying the washing liquid again into said reaction tube to fill the test tube with the washing liquid; and
   discharging said washing liquid out of said test tube at a second rate which is smaller than the first rate to such an extent that a drop of the washing liquid does not remain on the inner wall of the test tube.

2. A method according to claim 1, wherein the method further comprises a step of flowing an air through said reaction tube after discharging the washing liquid at the second rate.

3. A method according to claim 2, wherein the washing liquid is discharged out of the reaction tube at said first rate by means of a vacuum pump and the washing liquid is discharged out of the test tube at the second rate by means of a rolling pump.

4. A method according to claim 3, wherein the air flow is passed through the reaction tube by coupling the reaction tube with said vacuum pump.

5. A method according to claim 1, wherein after discharging the washing liquid at the first rate, the washing liquid is supplied into the test tube by means of the same nozzle from which the washing liquid is supplied like a shower.

6. A method according to claim 1, wherein the washing liquid is discharged out of the test tube at the second rate by means of a vacuum pump.

7. A method according to claim 1, wherein said reaction tube has a U-shaped having a thick cup portion and a thin non-cup portion and the washing liquid is supplied into the test tube like a shower via the thick cup portion and is discharged out of the test tube via the thin non-cup portion.

* * * * *